United States Patent [19]

Sydor

[11] Patent Number: 5,241,704
[45] Date of Patent: * Sep. 7, 1993

[54] BACK SUPPORT

[75] Inventor: Robin M. Sydor, Robbinsdale, Minn.

[73] Assignee: Ergodyne Corporation, St. Paul, Minn.

[*] Notice: The portion of the term of this patent subsequent to Sep. 22, 2009 has been disclaimed.

[21] Appl. No.: 872,440

[22] Filed: Apr. 23, 1992

Related U.S. Application Data

[63] Continuation-in-part of Ser. No. 689,980, Apr. 23, 1991, Pat. No. 5,148,549.

[51] Int. Cl.⁵ .................... A41D 13/04; A61F 5/02
[52] U.S. Cl. ............................... 2/44; 2/92; 2/338; 450/155; 128/876; 602/19
[58] Field of Search ............... 2/1, 2, 44, 92, 310, 2/311, 312, 338; 450/154, 155; 128/95.1, 99.1, 100.1, 101.1, 869, 845, 875, 78, 69, 87 R, 876; 602/819

[56] References Cited

U.S. PATENT DOCUMENTS

| | | | |
|---|---|---|---|
| 184,153 | 11/1876 | Holton | 450/155 |
| 468,425 | 2/1892 | Matthews et al. | |
| 472,086 | 4/1892 | Town | 2/44 |
| 572,465 | 12/1896 | Woolfolk et al. | 450/155 |
| 657,133 | 9/1900 | Redick | 450/15 |
| 811,167 | 1/1906 | Paddock | 2/92 |
| 933,610 | 9/1909 | Yanowsky | 450/15 |
| 934,625 | 9/1909 | Petrel | 450/155 X |
| 1,006,862 | 10/1911 | McCormick | 450/155 X |
| 1,006,863 | 10/1911 | McCormick | 450/155 X |
| 1,469,069 | 9/1923 | Freedenberg | 450/155 X |
| 1,565,808 | 12/1925 | Levy | 450/155 X |
| 1,768,223 | 6/1930 | Von Halle | 450/155 |
| 1,776,864 | 9/1930 | Cameron | |
| 1,983,636 | 12/1934 | Palkens | 450/155 X |
| 2,104,699 | 1/1938 | O'Dell | 128/78 |
| 2,282,021 | 5/1942 | Benningfield | 128/100 |
| 2,426,931 | 9/1947 | Holt | 450/155 X |
| 2,461,208 | 2/1949 | Goforth | 128/96 |
| 2,749,550 | 6/1956 | Pease | 2/41 |
| 2,813,526 | 11/1957 | Beebe | 128/78 |
| 2,840,822 | 7/1958 | Ericsson | 450/155 X |
| 2,981,258 | 4/1961 | Moellendorf | 128/527 |
| 3,052,236 | 9/1962 | Schrieber | 128/78 |
| 3,101,718 | 8/1963 | Rocker | 128/520 |
| 3,116,735 | 1/1964 | Geimer | 2/44 X |
| 3,298,366 | 1/1967 | Moore et al. | 450/155 X |
| 3,441,027 | 4/1969 | Lehman | 128/578 |
| 3,521,623 | 7/1970 | Nichols et al. | 128/78 |
| 3,554,190 | 1/1971 | Kaplan | 2/44 X |
| 3,603,316 | 9/1971 | Lehman | 128/546 |
| 3,605,731 | 9/1971 | Tigges | 128/24 |
| 3,623,488 | 11/1971 | Nakayama | 128/549 |
| 3,754,549 | 8/1973 | Nelkin | 128/100 |
| 3,920,008 | 11/1975 | Lehman | 128/96 |

(List continued on next page.)

FOREIGN PATENT DOCUMENTS

| 0055238 | 6/1982 | European Pat. Off. | 2/92 |
|---|---|---|---|
| 0615269 | 1/1927 | France | 450/155 |

OTHER PUBLICATIONS

English translation of French Patent No. 2,597,332.
*CompVest Back Support* Brochure, 1984 of Comp Equipment Corporation (now known as Ergodyne Corporation).
European Search Reoprt EP 91 10 1967.

*Primary Examiner*—Clifford D. Crowder
*Assistant Examiner*—Jeanette E. Chapman
*Attorney, Agent, or Firm*—Merchant, Gould, Smith, Edell & Welter

[57] ABSTRACT

A back support (110 & 210) for providing abdominal and lumbosacral support having a waistband (111 & 211) comprising a front panel (112 & 212) and a second panel (113 & 213). An elastic band (150 & 151) is operatively connected to the waistband (111 & 211). In one embodiment, the front panel (210) forms a cup to lift and support the fat tissue of an obese wearer.

14 Claims, 9 Drawing Sheets

U.S. PATENT DOCUMENTS

| | | | |
|---|---|---|---|
| 3,931,816 | 1/1976 | Waldmann | 450/155 X |
| 4,108,149 | 8/1978 | Castiglia | 450/155 |
| 4,325,379 | 4/1982 | Ozbey | 128/540 |
| 4,545,370 | 10/1985 | Welsh | 128/78 |
| 4,572,167 | 2/1986 | Brunswick | 128/78 |
| 4,709,692 | 12/1987 | Kirschenberg et al. | 128/78 |
| 4,768,499 | 9/1988 | Kemp | 128/78 |
| 4,782,535 | 11/1988 | Yewer, Jr. et al. | |
| 4,836,194 | 6/1989 | Sebastian et al. | 128/78 |
| 4,866,789 | 9/1989 | Dorm | 2/92 X |
| 4,881,528 | 11/1989 | Scott | 128/75 |
| 4,907,576 | 3/1990 | Curlee | 128/78 |
| 4,981,307 | 1/1991 | Walsh | 2/44 X |
| 4,993,409 | 2/1991 | Grim | 128/78 |
| 5,007,412 | 4/1991 | DeWall | 2/44 X |
| 5,038,760 | 8/1991 | Osborn | 128/78 |
| 5,040,524 | 8/1991 | Votel et al. | 128/95.1 X |
| 5,070,866 | 12/1991 | Alexander et al. | 128/78 |
| 5,147,261 | 9/1992 | Smith et al. | 2/338 X |
| 5,148,549 | 9/1992 | Sydor | 2/44 |

BACK SUPPORT

This is a continuation-in-part of U.S. patent application Ser. No. 07/689,980, filed Apr. 23, 1991, entitled "Back Support with Side Openings and Attached Apron" now U.S. Pat. No. 5,148,549.

BACKGROUND OF THE INVENTION

1. Field of the Invention

This invention relates generally to back supports and more particularly to a back support designed to provide two points of entry, thereby allowing side entry to the back support, and also greater adjustability. Further, the invention relates to a back support designed for obese persons.

2. Description of the Prior Art

The present invention is for use by persons who do relatively heavy or awkward lifting, pulling or pushing, and is primarily to help prevent serious back injury by providing abdominal and lumbosacral support. It is not intended to be a therapeutic device for persons who have previous back problems or abdominal muscle injury, although it can be used to help prevent the reoccurrence of such problems. The invention is particularly useful in hospitals or nursing homes by nurses or orderlies or the like who, from time to time, might have to lift or pull up patients or residents and need some support to prevent back problems from occurring, yet during the normal course of their other daily activities, they do not need this aid. They have the need for this type of support device occasionally, so want it handy as the need arises, and also need to be comfortable while wearing the device when not needed for support. Similar applications are to be found for industry use and for workers in other trades and industries.

Specifically, the present invention can readily be adapted for use by workers which need not only the benefit of the prevention of back injury, but also would like to wear a support which is not as readily visible to others. Still further, more adjustability is available to the wearer by having two points of entry. If the wearer's body is not symmetrical, such as the hips being offset, both sides of the support may be adjusted.

There are a number of stress band type devices which have been used over the years as therapeutic devices for helping to cure various aches and pains due to muscle or other type of damage, and particularly with respect to back problems. Many of these earlier devices are constructed so that they can not be conveniently removed or unfastened and then re-fastened from time to time as the need for the added support comes and goes. In other words, they must be worn full-time or not at all. Still others are bulky and/or cumbersome and/or fairly heavy and if used or worn as an outer garment, interfere with the normal working activities of the users. Other problems with the prior art involve complications in hook up and adjustment, cleaning and not being universal for different sizes and shapes.

For the past several years, the assignee of the present application, Ergodyne Corporation, has sold a back support which has addressed and solved many of the above-noted problems. The support is easy to use, adjustable for many different sizes, easily cleaned, and does not interfere with normal activity. It can readily be temporarily tightened for support when needed and released when normal activities occur.

While the above-mentioned back support has found great popularity and has provided for a much improved product, there are still several areas of concern relating not only to the assignee's back support but others presently available.

When such back supports have been worn by females, the support has tended to ride up on the female during use. While this has not been solely a problem for females, it has been typically been more of a problem for females due to the size of a female's hips in relationship to her waist. Typically, the hips tend to be larger in relationship to their waist. While this is of course not only a characteristic of females, females do tend to have this body shape more often than men. Accordingly, when used throughout this application, reference to females will not be limited to only females, but to persons having the more typical female body shape with respect to the hips in relationship to the waist. Also, depending on the activity engaged in by the wearer, a male may also have his support ride up while in use.

In addition, the elastic band of the back support has typically been secured by means which would not readily release the elastic band. Therefore, when an elastic band was faulty, it was necessary to replace the whole back support. In addition, it has been quite popular to now have a logo or other writing on the elastic band as that is what is visible. When ordered by different companies, they will quite often want their own logo on the elastic band. By previous methods of construction, it was necessary to keep in stock the combination of waistband and elastic band. Applicants have found by having the elastic band removable, the same waistband may be used by many elastic bands having various logos.

Still further, the back supports to date, while comfortable, have tended to be made of a textile material, and have not had efficient transfer of heat and moisture from the wearer of the back support. Still further, for industrial workers using tools, which are normally carried on a tool belt, back supports have not been popular as there have been the necessity of not only wearing a tool belt, but also the back support. This has proved cumbersome and the workers have tended not to wear both. U.S. Pat. No. 4,782,535 does show a belt, typically worn by weight lifters, which has been adapted to hold tools. However, the tools are supported directly from the strap webbing. The back support disclosed in U.S. Pat. No. 5,040,524, issued Aug. 20, 1991, and entitled "BACK SUPPORT", addresses many of these problems.

In a number of service industries, such in hotels and cruise liners, the wearer of the back support would like for the back support to be as hidden as possible. This provides for a neater appearance when not in use. The present invention addresses problems associated with the prior art and does provide for a back support which has two points of entry and has a "cummerbund" style which presents a cleaner and neater appearance. Still further, in another embodiment of the invention, a back support is provided for an obese person. The front section of the support is designed to provide a cupping action designed to capture and lift fat tissue for maximum abdominal support.

The present invention addresses the problems associated with the prior art devices.

SUMMARY OF THE INVENTION

The invention is a back support for providing abdominal and lumbosacral support as needed by the wearer. The support includes a waistband of a construction having a limited amount of stretch. The waistband includes a front panel having first and second ends and inner and outer surfaces and a second panel having first and second ends and inner and outer surfaces. The first end of the front panel is operatively connected to the first end of the second panel and the second end of the front panel is operatively connected to the second end of the second panel. An elastic band operatively connects the outer surface of the front and second panels. The elastic band has first and second ends releasably connected to the outer surface of the front panel so as to be easily moved between an unstretched and a stretched position.

In another embodiment, the invention is a back support for providing abdominal and lumbosacral support as needed by an obese wearer having a waistband of a construction having a limited amount of stretch. The waistband includes a front panel having first and second ends and inner and outer surfaces and a second panel having first and second ends and inner and outer surfaces. The first end of the front panel is operatively connected to the first end of the second panel and the second end of the front panel is operatively connected to the second end of the second panel. An elastic band is operatively connected to the outer surfaces of the front and second panels. The elastic band has first and second ends releasably connected to the outer surface of the front panel, so as to be easily moved be an unstretched and a stretched position. The front panel defines a convex portion proximate its center, wherein the convex portion cups and lifts and supports fat tissue of the obese wearer to provide increased abdominal support.

DETAILED DESCRIPTION OF THE PREFERRED EMBODIMENT

Figure 1:
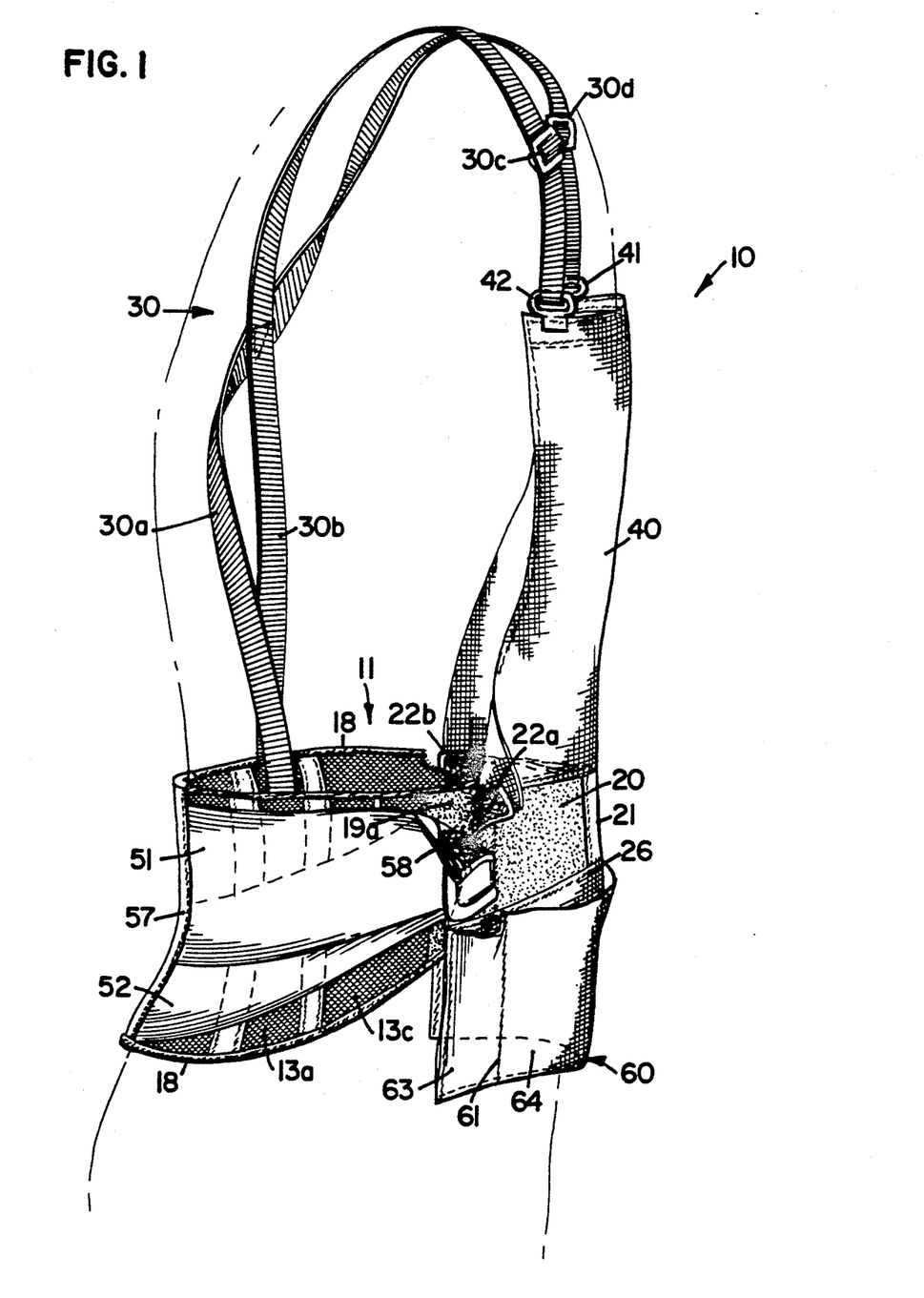
FIG. 1 is a perspective view of the back support of the present invention with a portion of the wearer being shown in phantom.

Referring to the drawings, wherein like numerals represent like parts throughout the several views, there is generally disclosed at 10 a back support. The back support 10 includes a waistband 11 having a front panel 12 and a second panel 13. While the combination of the front panel 12 and second panel 13 is referred to as a waistband, it is understood that the waistband 11 is designed to rest below the navel and accordingly, is not defined as being literally a band around the waist, but also may be below the waist. A piece of fabric is cut to the size of the second panel 13 and front panel 12. Depending upon the embodiment of the invention to be constructed, the fabric may be of either a stretchable or unstretchable fabric. As will be discussed more fully hereafter, in one embodiment it is desired to have some stretchability to the waistband 11, while in other embodiments, such as when heavy objects are to be positioned in the pockets, it is desirable to not have any stretch to the waistband 11. If stretchable materials are desired, a suitable material, such as Spandex ®, may be utilized. If it is desired to be non-stretchable, any suitable material, such as Apex, may be utilized. A plurality of semi-rigid stays 15 are secured to the second panel 13. On the inside of the second panel 13, next to the wearer, the stays 15 are covered by a rubberized elastic fabric and on the outside by a vinyl fabric. As shown in FIG. 1, two stays 15 are utilized on each half of the second panel 13. A ribbing or binding 18 is stitched across the top and bottom of the entire second panel 13. Loop fabrics 19a and 19b are stitched to the outside of the right and left of the second panel 13.

Figure 2:
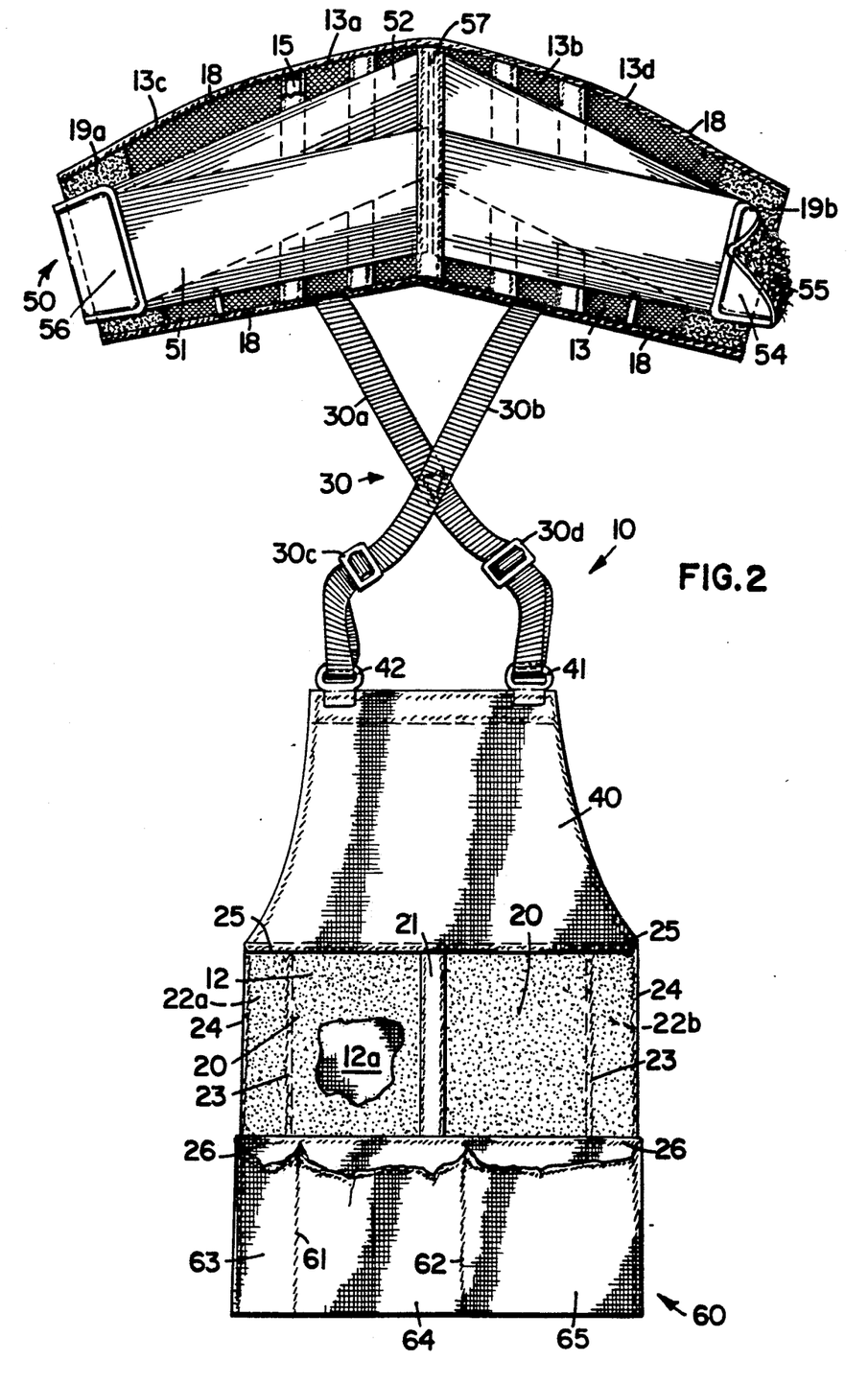
FIG. 2 is a plan view of the support shown in FIG. 1 showing the top surface of the support, with the support being positioned in a generally horizontal plane.

The front panel 12 is generally rectangular in shape and is constructed from a fabric 12a similar to the fabric used to construct the second panel 13. On the outside surface of the front panel 12, a loop fabric 20 is stitched. A vinyl member 21 is vertically stitched between each half of the front panel 12. The vinyl member is used to cover the stitching between each half of the panel 12. Alternately, only a single piece of fabric 20 may be used, thereby eliminating the need for vinyl member 21. On the inside of the front panel 12, rectangular shaped pieces of hook material 22a and 22b are stitched, on the right and left sides respectively, to the underneath side of the front panel 12. The stitching 23, 24, 25 and 26, which stitches the material 22a and 22b to the panel 12, is best seen in FIG. 2 and generally defines a rectangle. The hook materials 22a and 22b and loop fabrics 19a, 19b and 20 may be of any type well known in the industry which would form a hook and loop type fastener such as Velcro ® brand. The fabric utilized to construct the front panel 12 and second panel 13 may be somewhat stretchable, however, the loop fabrics 19a, 19b and 20 are substantially non-stretchable. The fabric for the front and second panels may be any suitable material such as a stretchable Spandex ® material. The binding 18 may be made of a suitable material such as tricot. A previously stated, if a stretchable material such as Spandex ® is utilized, the overall waistband will have some stretchability. For instance, with a waistband 11 having an overall length of approximately 42 inches, the waistband 11 may expand from one half to three inches and preferably from one and one half to two inches. This allows the waistband 11 to have the capabilities of stretching and conforming to the body of the wearer.

The second panel 13 has a right half 13a and a left half 13b. The right half has a bottom edge 13c and the left half has a bottom edge 13d. As can be seen in the drawings, the right half 13a and the left half 13b form a generally V-shaped second panel 13. Adjustable suspenders, generally designated as 30, are secured to the top edge of the second panel 13 at one end and to the top edge of the apron member 40 at their other end. The suspenders 30 include a first strap 30a and a second strap 30b. Two loop members 41 and 42 are stitched to the top of the apron 40 and one of the straps 30a and 30b positioned through the loops 41 and 42 respectively. Adjustable buckles 30c and 30d are operatively connected to the straps 30a and 30b, thereby allowing the length of the straps to be adjusted. It is of course understood that other suitable means of similarly connecting the front panel 12 to the second panel 13 may be utilized.

A four inch wide elastic band, generally designated as 50, has a top four inch band 51 and a bottom four inch band 52. The top band 51 is generally rectangular but has a slight V shape and the bottom band 52 has more of a V shape. The bands 51 and 52 are connected to each other at their ends by suitable means such as stitching. The left ends of the bands 51 and 52 have a vinyl piece 54 positioned on the outside surface and a hook material 55 fastened on the bottom surface. Similarly, the right ends are connected and have a vinyl piece 56 on the outside surface and a loop material 58 underneath. The bands 51 and 52 are held in place, proximate their middle, to the second panel 13 by a rectangular fabric piece 57 which is stitched to the second panel 13. The bands 51 and 52 are positioned between the fabric 57 and the panel 13. Alternative embodiments of similarly connecting the elastic bands 51 and 52 to the panel 13 may be utilized, such as those disclosed in U.S. Pat. No. 5,040,524, issued Aug. 20, 1991, and is hereby incorporated by reference. Each of the bands 51 and 52 may be of any suitable length, such as approximately 24 inches when not stretched. When stretched, this length may be increased to a suitable length so as to provide the necessary support. While the specific design of the support will dictate the length of the stretch desired, it has been found that from 5 to 15 inches and preferably from about 9 to 13 and still more preferably 10 to 12 inches of stretch is desirable.

An apron portion 40 is operatively connected, such as by stitching, to the top of the front panel 12. Since the front panel 12 is positioned proximate the waist, the apron 40 would cover the upper body portion of the wearer. If made from a cloth type material, the apron 40 would protect the wearer from liquid spills, as well as dirt and grease. The apron 40 could also be made from a variety of specialized material to form a special protective barrier to protect the wearer.

A pocket member 60 is operatively connected to the bottom of the front panel 12, by suitable means such as stitching. A piece of fabric may simply be folded upward and then stitched along two seams 61 and 62 to form three open top pockets 63, 64 and 65. Of course, it is understood that other suitable means may be utilized to form pocket members which would depend from the lower portion of the front panel 12.

It has further been found that it is sometimes desirable to have the front panel 12, pocket member 60 and apron member 40 disposable. The pocket member 60 may tend to wear out after use and the apron member 40 may tend to become soiled. The second panel 13 and elastic band 50 tend not to wear out as quickly. Accordingly, it would be advantageous to have the entire front portion replaceable or disposable. One convenient way of doing so would be to have the loops 41 and 42 clipped onto the apron member 40 instead of being stitched. Then, the loop members 41 and 42 could simply be unclipped and a new front portion (pocket member 60, front panel 12 and apron member 40) clipped to the loop members 41 and 42.

In operation, the wearer places the suspenders 30 over her shoulders so that the right side 13a is on her right side and the left side 13b is on her left side. When the suspenders are placed over the wearer's head, the front panel 12 is not attached to the second panel 13. That is, the support 10 is separated, as shown in FIG. 2. When putting the suspenders 30 over her shoulders, the elastic band 50 typically will have its hook materials 55 and 58 secured to the loop materials 19a and 19b so that the band 50 would appear as in FIG. 2, without having the end 55 turned up. Then, the wearer would release the ends of the elastic band 50 from the loop materials 19a and 19b. The right side 13a would then be pulled toward the right side of the front panel 12 and the hook material 22a would be placed on top of the loop material 19a. Then, the left side 13b would be brought toward the left side of the front panel 12 and the hook material 22b is then placed on top of the loop material 19b, thereby operatively connecting the front panel 12 to the second panel 13. Then, the wearer grasps each end of the elastic band by grasping each end of the vinyl tabs 54 and 56 and stretches the elastic band slightly so that the hook material 55 and 58 contacts the loop material 20.

The wearer then continues to wear the back support with the elastic band 50 having its ends attached to the loop material 20 in a substantially unstretched state. Alternately, the ends could be allowed to hang loose. Then, just before lifting, the ends of the elastic band 50 are grabbed at the vinyl tabs 54 and 56 and stretched as far forward as possible, and then placed against the fabric 20 so that the hook material 58 on the right side and the hook material 55 on the left side fastens the elastic band 50 in a stretched position. FIG. 1 shows the support 10 on a wearer. The V-shaped waistband is able to be worn by the wearer without having the support ride up as the wearer continues to wear the support 10.

The apron member 40 provides for needed protection in various industries, such as the health care industry where the wearer's clothing may become damaged or soiled. The apron will protect the wearer's clothing from splashes and/or dirt and other contaminants.

Still further, the support 10 has a pocket member 60 which allows for the wearer to have access to pockets. With the prior art devices, the support 10 would typically cover up the pockets on the normal clothing of the wearer. The pocket member 60 provides pockets which are quite often necessary for the wearer, especially in the health care industry.

A second embodiment of the invention is shown in FIGS. 3-8. The construction of the components of the back support 110 shown in FIGS. 3-8 is very similar to that of the back support 10. The specific details of construction will not be restated here unless they differ from the back support 10.

Figure 3:
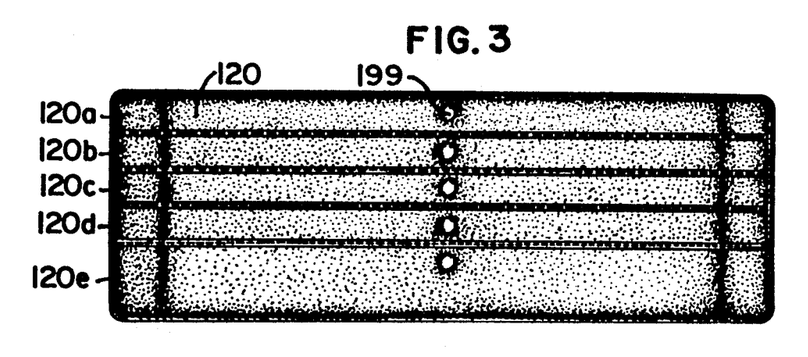
FIG. 3 is a front plan view of the front panel of the second embodiment of the present invention, showing the outer surface.
Figure 4:
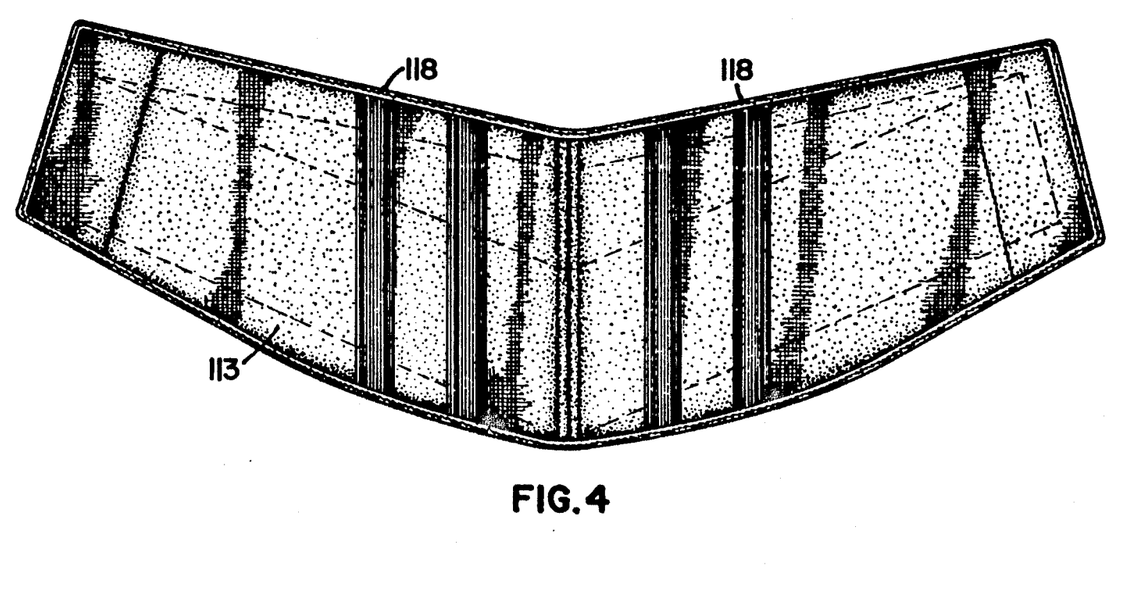
FIG. 4 is a front plan view of the back panel of the second embodiment showing the inner surface.
Figure 5:
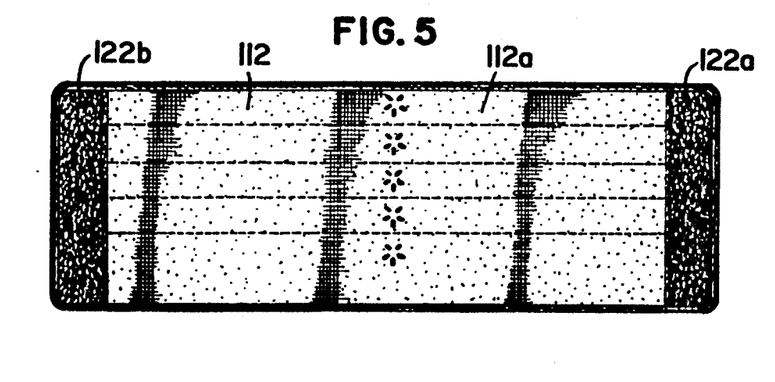
FIG. 5 is a front plan view of the front panel of the second embodiment showing the inner surface.
Figure 6:
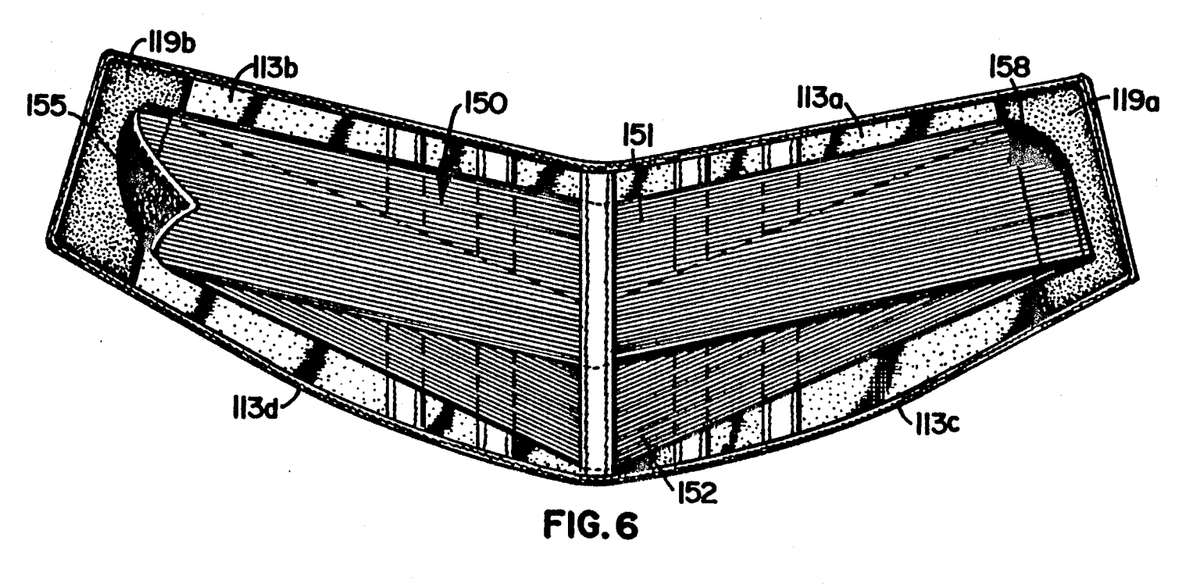
FIG. 6 is a front plan view of the second embodiment showing the outer surface of the back panel.

The back support 110 includes a waistband 111 having a front panel 112 and a second panel 113. A plurality of semi-rigid stays 115 are secured to the second panel 113. A ribbing or binding 118 is stitched across the top and bottom of the entire second panel 113. Loop fabrics 119a and 119b are stitched to the outside of the right and left sections of the second panel 113. The front panel 112 is generally rectangular in shape and is constructed from a fabric 112a similar to the fabric used to construct the second panel 113. On the outside surface of the front panel 112, a loop fabric 120 is stitched. On the inside of the front panel 112, rectangular shaped pieces of hook material 122a and 122b are stitched, on the right and left sides respectively, to the underneath side of the front panel 112. The loop fabric 120, as best seen in FIG. 3, comprises five separate strips 120a, 120b, 120c, 120d and 120e. These separate strips are sewn on the front panel 112 by stitching or other suitable methods. The purpose of the separate strips is to provide the look of a cummerbund. The hook materials 122a and 122b and loop materials 119a, 119b, and 120 may be of any type well known in the industry which would form a hook and loop fastener, such as Velcro ® brand. The fabric utilized to construct the front panel 112 and second panel 113 may be somewhat stretchable, however, the loop fabrics 119a, 119b and 120 are substantially non-stretchable. The fabric for the front and second panels and binding 118 are similar to that of the first embodiment.

The second panel 113 has a right half 113a and a left half 113b. The right half has a bottom edge 113c and the left half has a bottom edge 113d. As has be seen from the drawings, the right half 113a and the left half 113b form a generally V-shaped second panel 113.

A four inch wide elastic band, generally designated as 150, has a top four inch band 151 and a bottom four inch band 152. The band 150 is substantially identical to the band 50 in the first embodiment and has hook material 155 fastened to both ends on the surface adjacent to the outside surface of the second panel 113. In addition, five buttons 199 are fastened by means well known in the art to the front panel 112. The buttons 119, along with the strips of loop material, provide for the appearance of a cummerbund.

Figure 7:
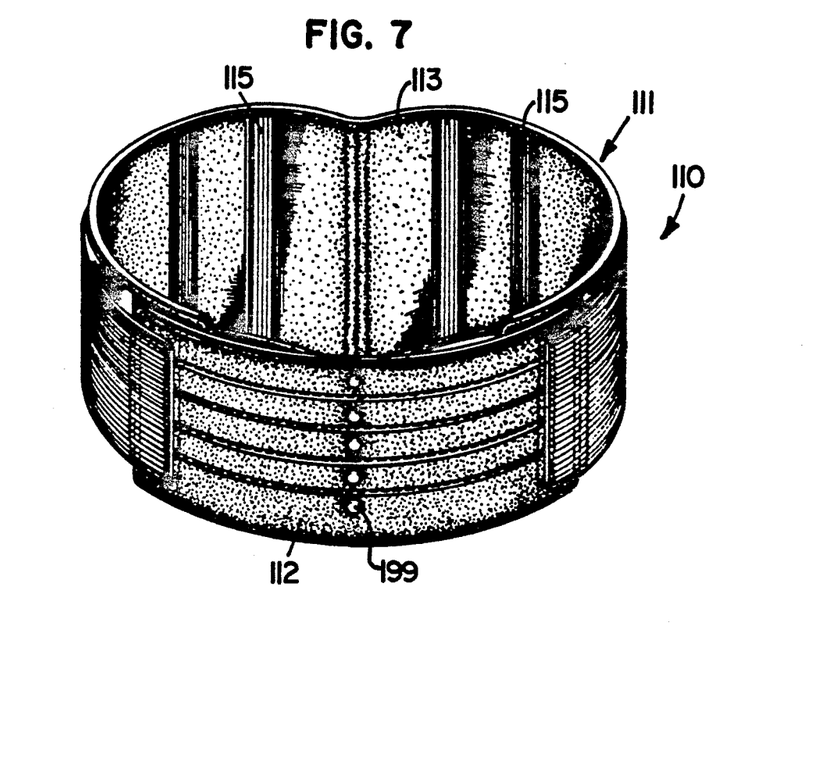
FIG. 7 is a perspective view of the second embodiment showing the elastic band in an unstretched position.
Figure 8:
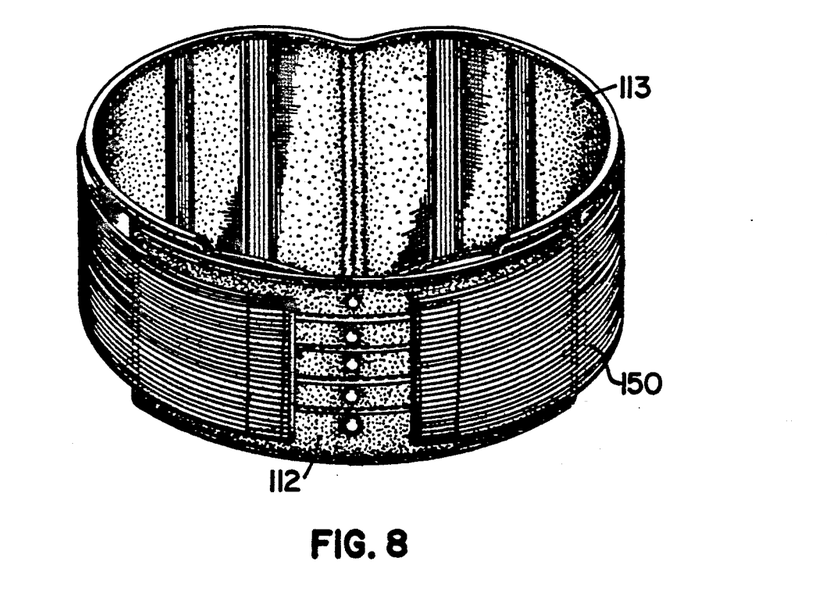
FIG. 8 is a perspective view of the second embodiment showing the elastic band in a stretched, supporting position.

As can be seen, the three main differences between the first and second embodiments are first that no suspenders are utilized, secondly that there is no apron and finally, that the front panel has a more stylized finish to give a cleaner or neater appearance. In viewing FIG. 7, this is how the back support 110 would appear when the elastic band 150 is not tightened to a supporting position. In the position as shown in FIG. 7, the major portion of the back support would be covered by a coat worn by the wearer. It is only the cummerbund style front portion of the front panel 112 which would be seen. Then, when support is needed, the elastic band 150 is stretched to the position shown in FIG. 8. There the elastic band 150 would be seen, but this would only be when the extra support is needed.

Figure 9:
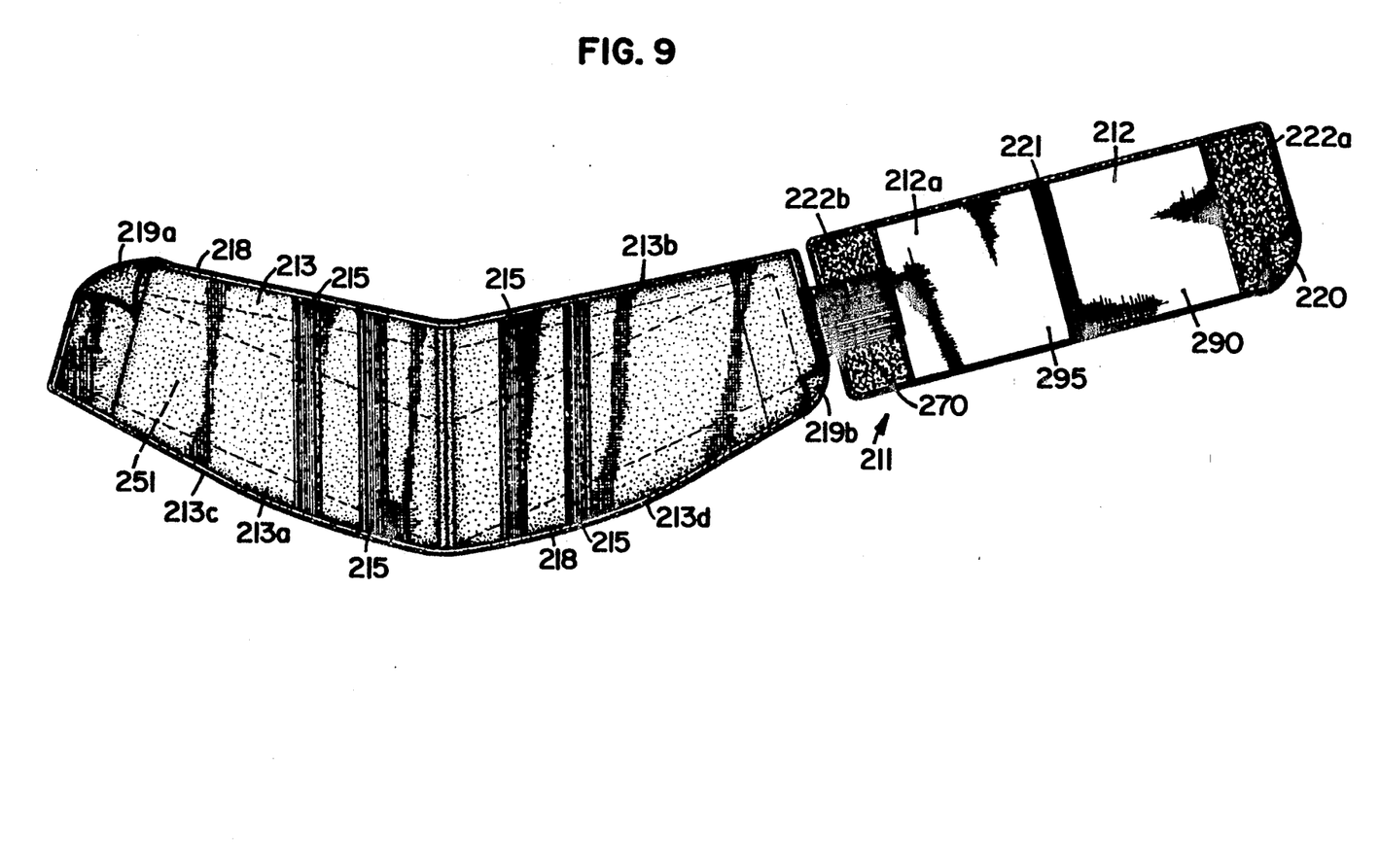
FIG. 9 is a plan view of a third embodiment of the present invention showing the inside surface.
Figure 10:
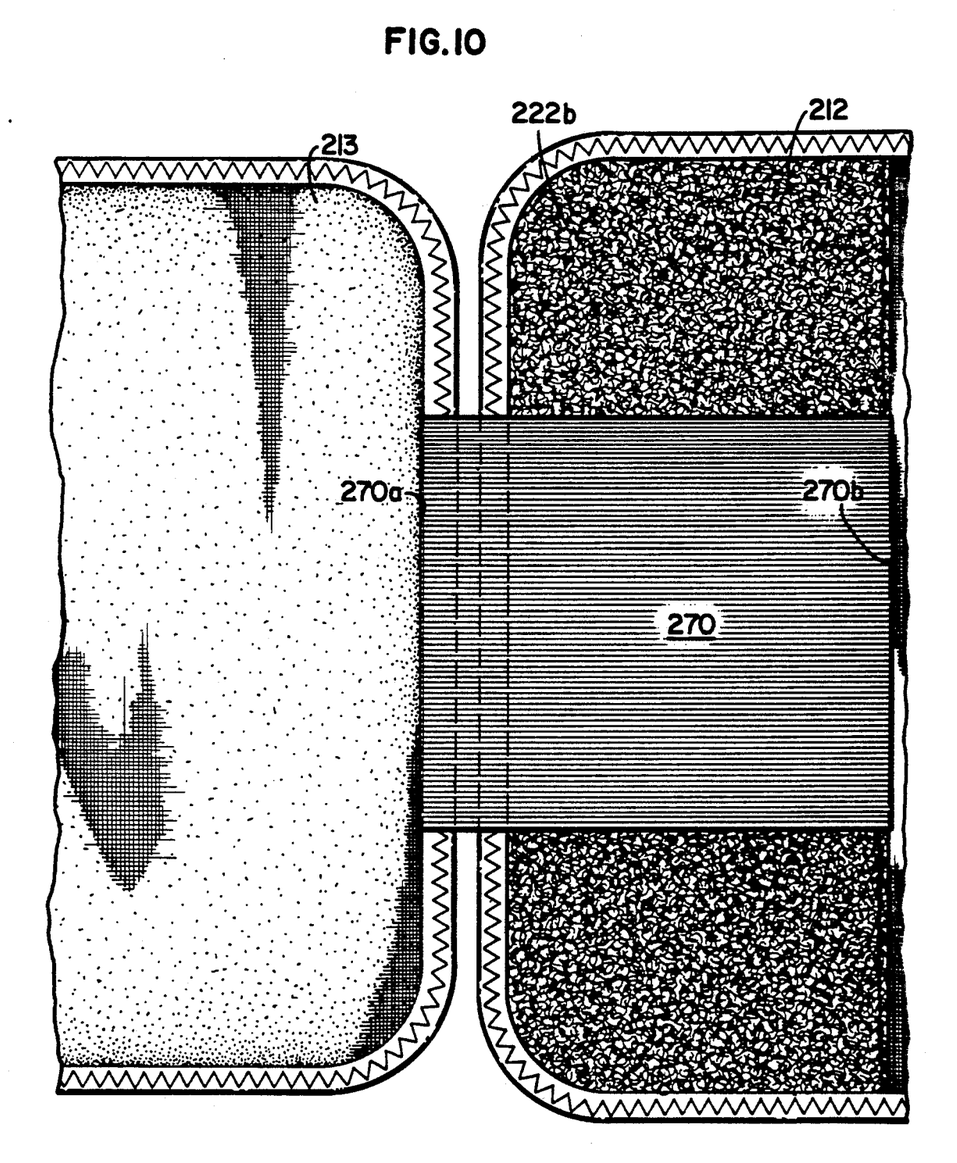
FIG. 10 is an enlarged fragmentary plan view of a portion of the embodiment shown in FIG. 9.

A third embodiment of the present invention is shown in FIGS. 9-13. The third embodiment is a back support which is designed for use by obese persons. The back support 210 includes a waistband 211 having a front panel 212 and a second panel 213. While the combination of the front panel 212 and the second panel 213 is referred to as a waistband, it is understood that the waistband 211 is designed to rest below the navel and accordingly, is not defined as being literally a band around the waist, but also may be below the waist. A piece of fabric is cut the size of the second panel 213 and the front panel 212. Depending upon the embodiment of the invention to be constructed, the fabric may be either stretchable or unstretchable fabric as discussed with respect to the first embodiment. A plurality of semi-rigid stays 215 are secured to the second panel 213. A ribbing or binding 218 is stitched across the top and bottom of the entire second panel 213. Loop fabrics are stitched to the outside of the right and left sections of the second panel 213. Again, similar to the second embodiment, the construction of many components of the third embodiment is similar to the first and will not be repeated here. In FIG. 9, the loop fabrics 219a and 219b are in the same locations as loop fabrics 19a and 19b and 119a and 119b.

The front panel 212 is generally rectangular in shape and is constructed from a fabric 212a similar to the fabric used to construct the second panel 213. On the outside surface of the front panel 212, a loop fabric 220 is stitched. The loop fabric covers substantially all of the front panel 212. A vinyl member 221 is vertically stitched between each half of the front panel 212. On the inside of the front panel 212, rectangular pieces of hook material 222a and 222b are stitched on the right and left sides respectively. The hook and loop materials are similar to that used in the other embodiments. The fabric used to construct the front panel 212 and second panel 213 may be somewhat stretchable, however, the loop fabrics are substantially non-stretchable. The fabric for the front and second panels may be any suitable material such as stretchable Spandex ® material and the binding may be made from suitable material such as Tricot ®.

Similar to the other embodiments, the second panel 213 has a right half 213a and a left half 213b. The right half has a bottom edge 213c and the left half has a bottom edge 213d. As can be seen from the drawing, the right half 213a and the left half 213b form a generally V-shaped second panel 213. A four inch wide elastic band 251 is similar to the bands 51 and 151 previously described.

An elastic strip 270 operatively loosely connects the front panel to the second panel. The elastic strip is approximately four inches in length and has a first end 270a stitched to the second panel 213 and a second end 270b stitched to the front panel 212. This elastic band 270 only loosely connects the two panels and the hook and loop fasteners are still utilized to secure the panels together. However, the elastic strip 270 aids in the positioning of the two panels when the back support 210 is being put on by the wearer. However, the elastic strip 270 does not secure the two panels tightly to each other. The hook and loop fasteners are utilized for this purpose. What the elastic strip 270 does do is allow for the back support to have the equivalent of two side entries while at the same time providing for a means of connecting the two panels loosely while it is being positioned about the wearer. The two points of entry are advantageous to allow for more adjustments for those situations where the wearer's body is not symmetrical.

Figure 11:
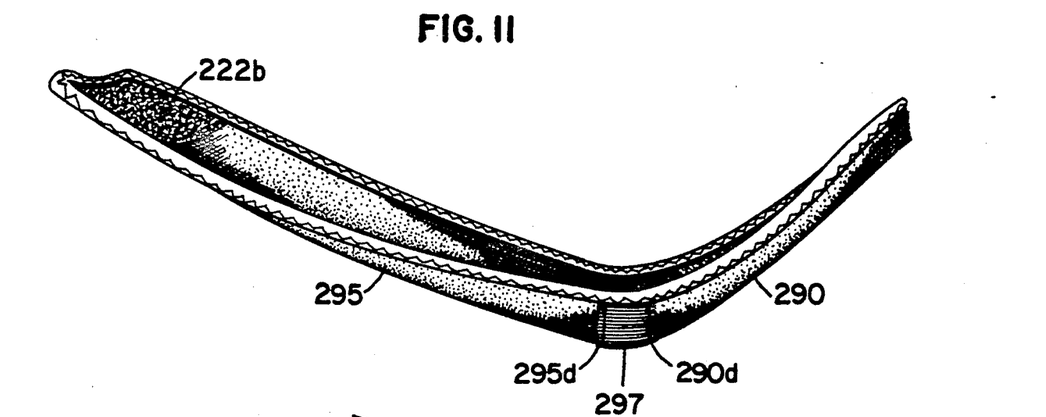
FIG. 11 is a perspective view of the front panel of the embodiment shown in FIG. 9.
Figure 12:
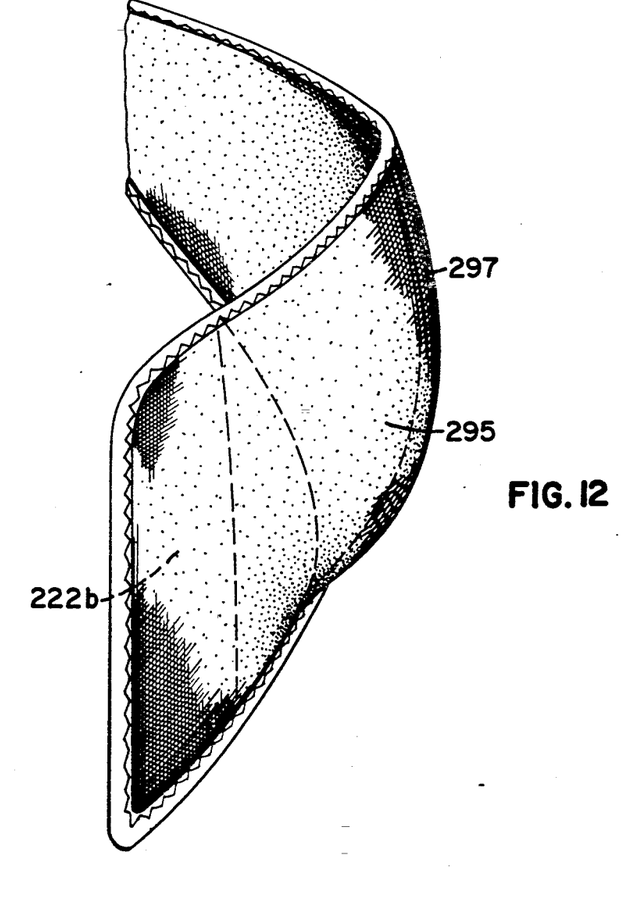
FIG. 12 is another perspective of the front panel of the embodiment shown in FIG. 9.
Figure 13:
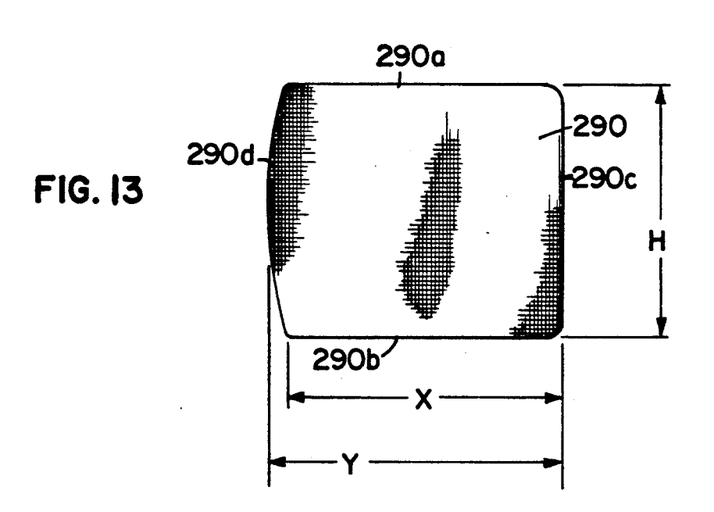
FIG. 13 is a front plan view of one section of the front panel shown in FIG. 9.

The front panel 212 comprises a first section 290 and a second section 295. The first section 290 is shown in FIG. 13. The other section 295 is a mirror image thereof and will not be described in more detail. The first section 290 is generally rectangular in shape and has a top edge 290a generally parallel to a bottom edge 290b. A right edge 290c is generally perpendicular to the top edge 290a and the bottom edge 290b. The left edge 290d is slightly curved outward away from the edge 290c. Thereby, the width of the section 290 is greater in the middle than at the top and bottom edges. The height "H" may be any suitable height, but in one embodiment, would be approximately nine and one-half inches. The length at the top and bottom, or the designation "X" in FIG. 13, is approximately eleven inches. The wider width at the center or "Y" is approximately eleven and three-fourths inches. Preferably, the extra width would be from three-fourths to one inch greater than the width at the edges. As viewed in FIG. 13, the panel 290 is generally planar before attachment to the other section 295. The edge 290d is operatively connected by suitable means, such as stitching, to a vinyl piece 297. A stay (not shown) may be positioned in the vinyl piece 297. Similarly, the edge 295d is likewise sewn to the vinyl strip 297, as best seen in FIG. 11. By having the edges 290d and 295d curved, a cup is formed when the two sections are sewn together to the vinyl strip 297. This cupping action, when worn, is around the wearer's larger abdomen and generally captures and lifts the fat tissue of the wearer for maximum abdominal support.

In operation, the second embodiment of back support 110 is substantially similar to the first embodiment, except for the lack of suspenders. One side of the front panel 112 is connected to the second panel 13 by having the hook material 122a connect to the loop materials 119a. Then, the second panel 113 is positioned around the wearer's back and the other side of the front panel 112 is connected to the back panel around the front of the wearer and the hook material 122b contacts the loop material 119b. Then, the wearer may make the final adjustments so that the front panel 112 and second panel 113 are comfortable around the wearer's midsection. If the wearer then wants additional support, the band 150 is stretched and moved to the position shown in FIG. 8 by initially releasing the band from the front panel 112 (as in FIG. 7) and extending it closer to the centerline of the front panel 112.

The operation of the third embodiment is also somewhat similar to that of the two previous embodiments.

The back section 213 is positioned around the back of the wearer and then the front section 212 is wrapped around the front of the wearer and hook material 222a comes in contact with the loop material 219a, thereby securing one end of the front panel 212 to the second panel 213. Then, the hook material 222b is moved over the loop material 219b and pressed down to firmly secure the support in position. The elastic band 270 maintains a loose connection between the one end of the second panel 213 and front panel 212 before the hook and loop material are fastened. The actual distance that the front panel overlaps the second panel will determined by the size of the wearer and the wearer can make the necessary adjustments so that it is comfortable. Then, the operation of the elastic band 251 is similar to the other embodiments and is stretched to provide additional support as previously discussed.

The front panel 212 has a convex portion proximate its center (around the vinyl strip 297). When in position, the convex portion cups the fat tissue of the obese wearer and lifts and supports the fat tissue to provide increased abdominal support. When the convex portion cups or cradles the fat tissue, not only is the abdominal support increased, but also the lower back support is also increased when the fat tissue is lifted and support.

The convex portion which is conformable to the fat tissue of the wearer is shown as being constructed from two generally flat, planar pieces of material. It is the curved edge which, when sewn together, provides for the cup configuration. It is of course understood that other suitable means of constructing such a cup may be utilized.

Other modifications of the invention will be apparent to those skilled in the art in light of the foregoing description. This description is intended to provide specific examples of individual embodiments which clearly disclose the present invention. Accordingly, the invention is not limited to these embodiments or the use of elements having specific configurations and shapes as presented herein. All alternative modifications and variations of the present invention which follow in the spirit and broad scope of the appended claims are included.

I claim:

1. A back support for providing abdominal and lumbosacral support as needed by the wearer, comprising:
   (a) a waistband of a construction having a limited amount of stretch, said waistband comprising:
      (i) a front panel having first and second ends and inner and outer surfaces;
      (ii) a second panel having first and second ends and inner and outer surfaces; and
      (iii) means for operatively connecting said first end of said front panel to said first end of said second panel and for operatively connecting said second end of said front panel to said second end of said second panel; and
   (b) an elastic band operatively connected to said outer surfaces of said front and second panels, said elastic band having first and second ends releaseably connected to said outer surface of said front panel, so as to be easily moved between an unstretched and a stretched position.

2. The support of claim 1, wherein said connecting means comprises hook material and loop material operatively connected to said front and second panels.

3. The support of claim 2, wherein said elastic band is operatively connected to said front panel with hook material and loop material.

4. The support of claim 3, further comprising:
   (a) first hook material operatively connected to said inside surface of said front panel proximate both first and second ends; and
   (b) first loop material operatively connected to said outside surface of said second panel proximate both first and second ends, said first hook material positioned to be engaged by said first hook material.

5. The support of claim 4, further comprising:
   (a) said elastic band having an inside surface and outside surface;
   (b) second loop material operatively connected to said outside surface of said front panel, said second loop material covering substantially all of said outside surface; and
   (c) second hook material operatively connected to said inside surface of said elastic band proximate both first and second ends.

6. A back support for providing abdominal and lumbosacral support as needed by the wearer, comprising:
   (a) a waistband of a construction having a limited amount of stretch, said waistband comprising:
      (i) a front panel having first and second ends and inner and outer surfaces;

(ii) a second panel having first and second ends and inner and outer surfaces; and (iii) means for operatively connecting said first end of said front panel to said first end of said second panel for operatively connecting said second end of said front panel to said second end of said second panel; and (b) an elastic band operatively connected to said outer surfaces of said front and second panels, said elastic band having first and second ends releaseably connected to said outer surface of said front panel, so as to be easily moved between an unstretched and a stretched position;

(c) first hook material operatively connected to said inside surface of said front panel proximate both first and second ends;

(d) first loop material operatively connected to said outside surface of said front panel proximate both first and second ends, said hook material positioned to be engaged by said first loop material;

(e) said elastic band having an inside surface and outside surface;

(f) second loop material operatively connected to said outside surface of said front panel, said second loop material covering substantially all of said outside surface; and (g) second hook material operatively connected to said inside surface of said elastic band proximate both first and second ends.

7. A back support for providing abdominal and lumbosacral support as needed by an obese wearer, comprising:

(a) a waistband of a construction having a limited amount of stretch, said waistband comprising:

(i) a front panel having first and second ends and inner and outer surfaces;

(ii) a second panel having first and second ends and inner and outer surfaces; and (iii) means for operatively connecting said first end of said front panel to said first end of said second panel and for operatively connecting said second end of said front panel to said second end of said second panel; and (b) an elastic band operatively connected to said outer surfaces of said front and second panels, said elastic band having first and second ends releaseably connected to said outer surface of said front panel, so as to be easily moved between an unstretched and a stretched position and (c) said front panel defining a convex portion proximate its center, wherein said convex portion cups and lifts and supports fat tissue of the obese wearer to provide increased abdominal support.

8. The back support of claim 7, said front panel further comprising:

(a) a right section;

(b) a left section, said left section operatively connected to said right section;

(c) said sections each having, before connecting, a generally flat configuration; and (d) said sections having generally parallel top and bottom edges; and an outer edge generally perpendicular to said top and bottom edges; and an inner edge wherein said section's width is greater at its center than at its top and bottom.

9. The back support of claim 8, wherein said section's width at its center is from ¾ to 1 inched wider than at its top and bottom.

10. The back support of claim 7, further comprising an elastic strip having a first end operatively connected to said front panel and a second end operatively connected to said second panel.

11. The support of claim 7, wherein said connecting means comprises hook material and loop material operatively connected to said front and second panels.

12. The support of claim 11, wherein said elastic band is operatively connected to said front panel with hook material and loop material.

13. The support of claim 12, further comprising:

(a) first hook material operatively connected to said inside surface of said front panel proximate both first and second ends; and (b) first loop material operatively connected to said outside surface of said second panel proximate both first and second ends, said first hook material positioned to be engaged by said first hook material 14. The support of claim 13, further comprising:

(a) said elastic band having an inside surface, outside surface, first end and second end;

(b) second loop material operatively connected to said outside surface of said front panel, said second loop material covering substantially all of said outside surface; and (c) second hook material operatively connected to said inside surface of said elastic band proximate both first an second ends.

* * * * *

UNITED STATES PATENT AND TRADEMARK OFFICE
CERTIFICATE OF CORRECTION

PATENT NO. : 5,241,704

DATED : September 7, 1993

INVENTOR(S) : Sydor

It is certified that error appears in the above-identified patent and that said Letters Patent is hereby corrected as shown below:

In column 2, line 53, after the word "such" please insert --as--.

In column 3, line 34, please delete "be" and substitute therefor --between--.

In column 4, line 64, please delete "A" and substitute therefor --As--.

In column 7, line 33, please delete "be" and substitute therefor --been--.

In column 8, line 14, please delete "is" and substitute therefor --are--.

In column 9, line 28, please delete "13" and substitute therefor --113--.

In column 9, line 68, please delete "support" and substitute therefor --supported--.

In column 10, line 52, please delete "hook" and substitute therefor --loop--.

In column 12, line 20, please delete "inched" and substitute therefor --inch--.

UNITED STATES PATENT AND TRADEMARK OFFICE
CERTIFICATE OF CORRECTION

PATENT NO. : 5,241,704
DATED : September 7, 1993
INVENTOR(S) : Sydor

It is certified that error appears in the above-indentified patent and that said Letters Patent is hereby corrected as shown below:

In column 12, line 39, please delete "hook" and substitute therefor --loop--.

Signed and Sealed this

Twelfth Day of April, 1994

Attest:

BRUCE LEHMAN

*Attesting Officer*   *Commissioner of Patents and Trademarks*